US00PP11466P

United States Patent [19]

Ito et al.

[11] Patent Number: Plant 11,466

[45] Date of Patent: Aug. 1, 2000

[54] ZOYSIA GRASS PLANT NAMED 'SS-500'

[75] Inventors: Minoru Ito; Roberto Guerra Amaral Gurgel, both of Itapetininga, Brazil

[73] Assignee: Sod Solutions, Inc., Mt. Pleasant, S.C.

[21] Appl. No.: 09/031,492

[22] Filed: Feb. 26, 1998

[51] Int. Cl.[7] ..... A01H 5/00

[52] U.S. Cl. ..... Plt./390

[58] Field of Search ..... Plt./390, 388

[56] References Cited

U.S. PATENT DOCUMENTS

| | | | |
|---|---|---|---|
| P.P. 5,845 | 12/1986 | Youngner | Plt./390 |
| P.P. 6,345 | 10/1988 | Whiting | Plt./390 |
| P.P. 6,516 | 1/1989 | Whiting | Plt./390 |
| P.P. 6,529 | 1/1989 | Pursley | Plt./390 |
| P.P. 7,074 | 12/1989 | Whiting | Plt./390 |
| P.P. 8,553 | 1/1994 | Staton | Plt./390 |
| P.P. 9,089 | 3/1995 | Yamagishi et al. | Plt./390 |
| P.P. 9,127 | 5/1995 | Giebault et al. | Plt./390 |
| P.P. 9,135 | 5/1995 | Giebault et al. | Plt./390 |
| P.P. 10,187 | 1/1998 | Yaneshita et al. | Plt./390 |
| P.P. 10,636 | 10/1998 | Engelke | Plt./390 |
| P.P. 10,778 | 2/1999 | Engelke | Plt./390 |
| 5,413,909 | 5/1995 | Bassam et al. | 435/6 |
| 5,643,479 | 7/1997 | Lloyd et al. | 219/137 |

OTHER PUBLICATIONS

Caetano–Anolles et al. "DNA Amplification Finger printing Using . . . " Jun. 1991, Bio/Technology vol 9. p. 553.

Bassam and Bentley "Electrophoresis of Polyester–Bodied Polyacrylamide Gels" BioTechniques 19:568 Oct. 1995.

Bassam et al. "Fast and Sensitive Silver Staining of DNA in Polyacrylamide Gels" Analytical Biochemistry 196:80 1991.

*Primary Examiner*—Howard J. Locker
*Assistant Examiner*—Wendy A Baker
*Attorney, Agent, or Firm*—Myers Bigel Sibley & Sajovec

[57] ABSTRACT

A new and distinct variety of *Zoysia japonica* turfgrass, called 'SS-500', is characterized by its color, long and wide leaf blades, large stolons, an open growth habit, and rapid establishment rate.

10 Drawing s

BACKGROUND OF THE INVENTION

The present invention relates to a new and distinct variety of a perennial Zoysia grass, discovered on a Brazilian turf farm in São Paolo during a routine field inspection. The grass was found in a production field of a common Brazilian grass known as 'Wild Zoysia' (unpatented). The new grass is believed to be a sport of 'Wild Zoysia' due to its color and its larger leaf size and longer node length compared to 'Wild Zoysia'. The novel grass, termed 'SS-500', was propagated asexually in São Paolo, Brazil. 'SS-500' is a distinct, asexually propagated variety of Zoysia grass. 'SS-500' is the varietal designation of this new grass. The name 'SS-500' may also designate this plant in commerce.

SUMMARY OF THE INVENTION

'SS-500' is a attractive green Zoysia grass, with an open growth habit. It is characterized by the combination of its color, open growth habit, and large leaf blade length and width.

DETAILED DESCRIPTION OF THE VARIETY

The following is a detailed description of the new Zoysia grass variety known as 'SS-500', based upon observations of the plant grown in plug trays and field plots. Color notations are based on *The Royal Horticultural Society Colour Chart*, The Royal Horticultural Society, London.

'SS-500' is a perennial, vegetatively propagated Zoysia grass, believed to be a variety of *Zoysia japonica*. The parent of 'SS-500' is believed to be a native Brazilian variety of *Zoysia japonica*, commonly known as 'Wild Zoysia'. 'SS-500' is a wide-bladed grass with an open growth habit. Applicants have asexually propagated 'SS-500' by means of stolons and rhizomes. Applicants have discovered the novelty and distinctness of 'SS-500' compared to other varieties of Zoysia.

'SS-500' has an open growth habit, large stolons and leaf blades, and a massive root system. Side-by-side comparisons of 'SS-500' to variety 'El Toro' (a standard for rapid growth of Zoysia) demonstrated that 'SS-500' exhibits rapid growth; complete coverage can occur within five to six months after planting, compared to 'El Toro' which takes nine to ten months under similar conditions. Each variety was planted in 8'×8' plots using 4-inch prerooted grass plugs planted 12-inches on center to determine coverage rates.

'SS-500' is characterized by its large leaf blade width and length, open growth habit and large stolon size, and other characteristics described herein. 'SS-500' has a rapid establishment rate, high tolerance to drought, good fall color retention rates, and good tolerance to herbicides MSMA and 2-4-D.

DIMENSIONS AND GROWTH HABIT

'SS-500' was discovered on a Brazilian turf farm in a production field of a common Brazilian grass known as 'Wild Zoysia'. The new grass was initially believed to be an 'off-type', or sport, of 'Wild Zoysia' due to its color and its larger leaf size (compared to 'Wild Zoysia'). 'SS-500' exhibits an open growth habit and large leaf width and length, compared to other Zoysia grasses. 'SS-500' is low growing during the initial stage of coverage. After the ground is covered the grass becomes upright and open in habit. The grass spreads by stolons and rhizomes that form an open uniform groundcover. The root structure of 'SS-500' is massive and deep, with large individual roots.

Figure 1:
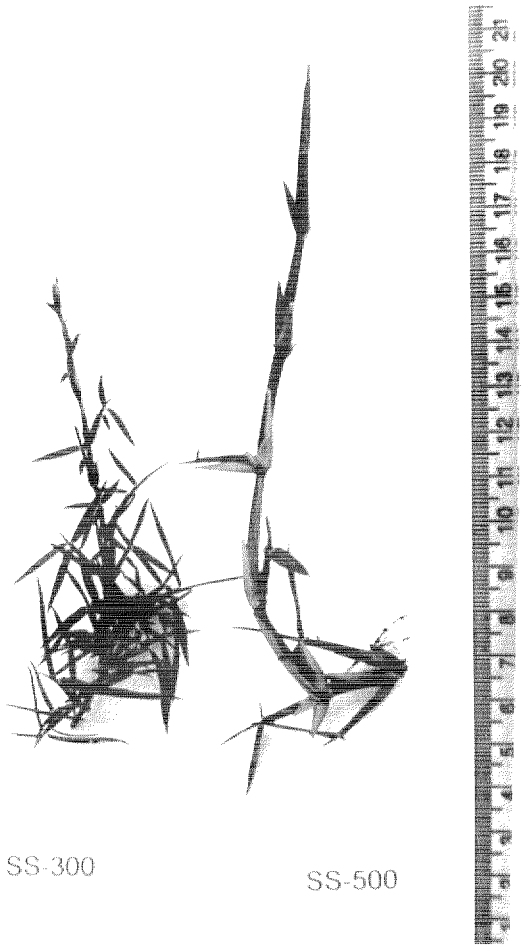
FIG. 1 compares stolons of 'SS-500' and 'SS-300'. 'SS-300' is another new variety of Zoysia grass, and is the subject of co-pending U.S. Plant Patent application Ser. No. 09/028,031. A metric ruler is provided for scale.
Figure 2:
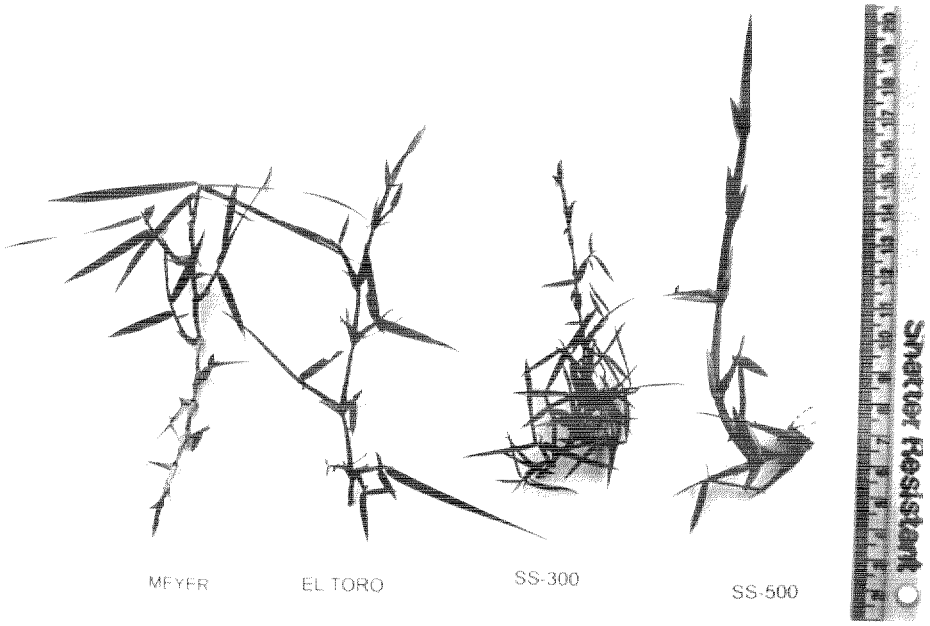
FIG. 2 compares stolons of 'SS-500' and Zoysia cultivars 'Meyer', 'El Toro', and 'SS-300', next to a metric scale.
Figure 3:
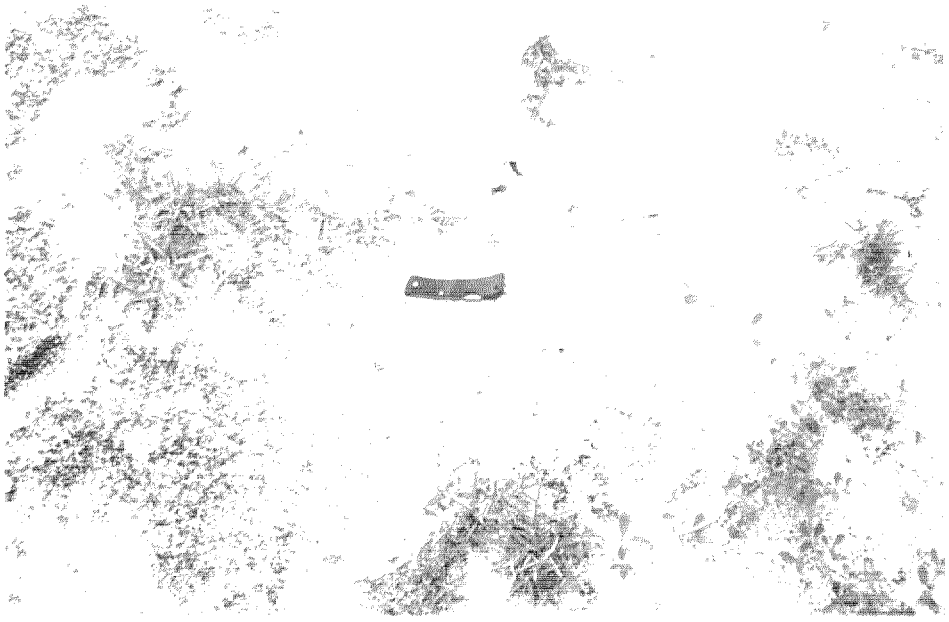
FIG. 3 shows a runner of 'SS-500' that grew to over 30 inches in less than a month.
Figure 4:
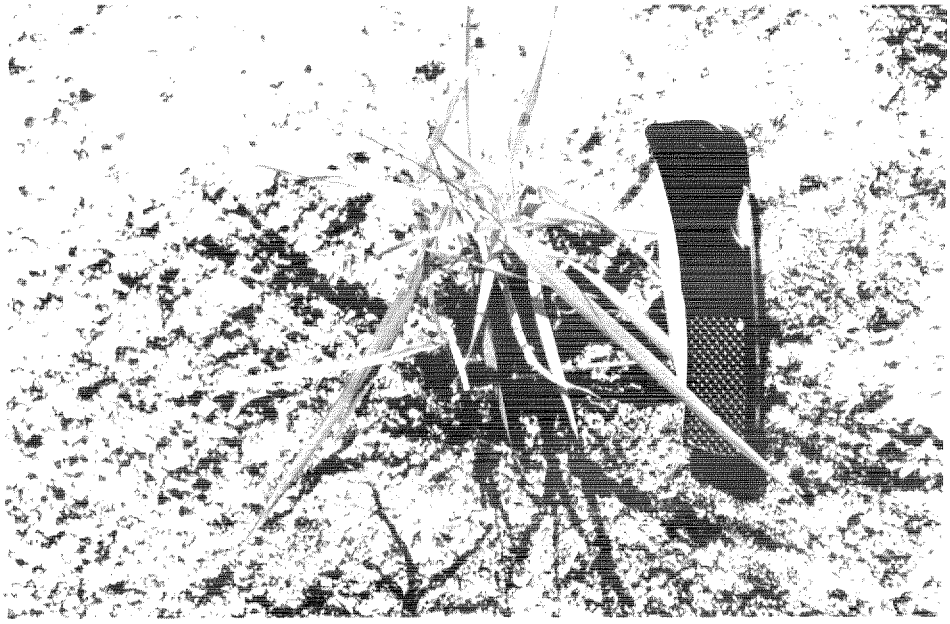
FIG. 4 shows a plug of 'SS-500'.
Figure 5:
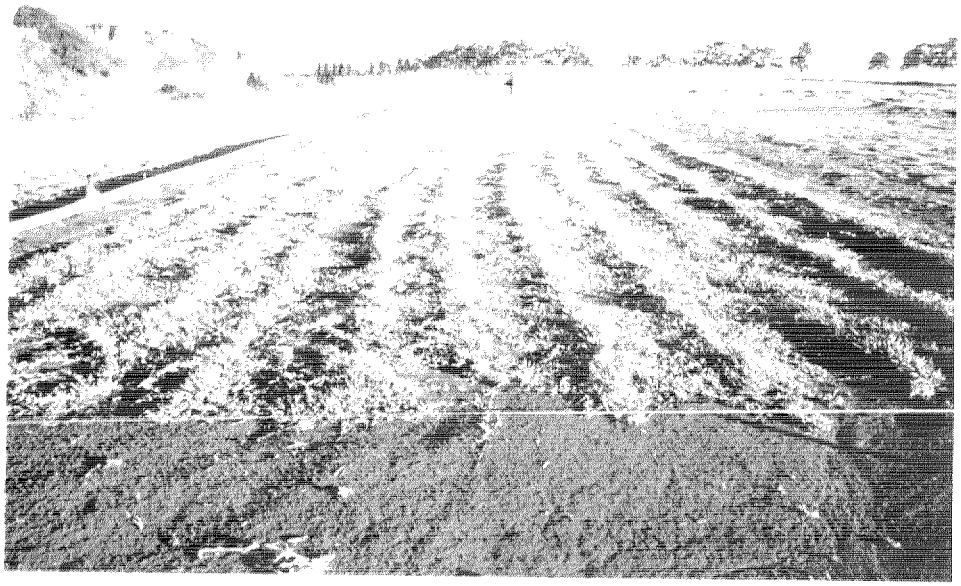
FIG. 5 shows 'SS-500' in the field at three months. Compare this to FIG. 6.
Figure 6:
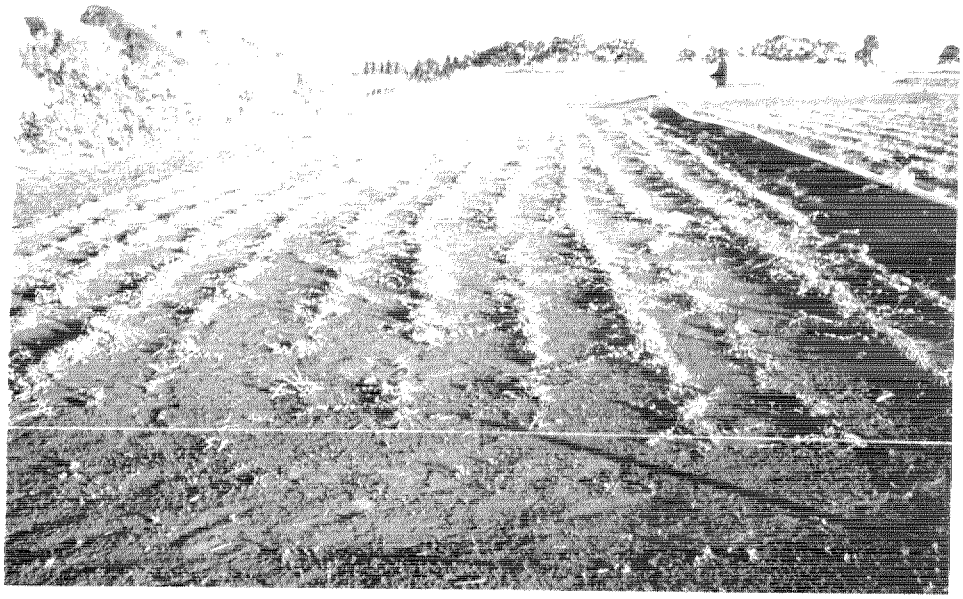
FIG. 6 shows 'El Toro' in the field at three months, grown under the same conditions as the 'SS-500' depicted in FIG. 5.
Figure 7:
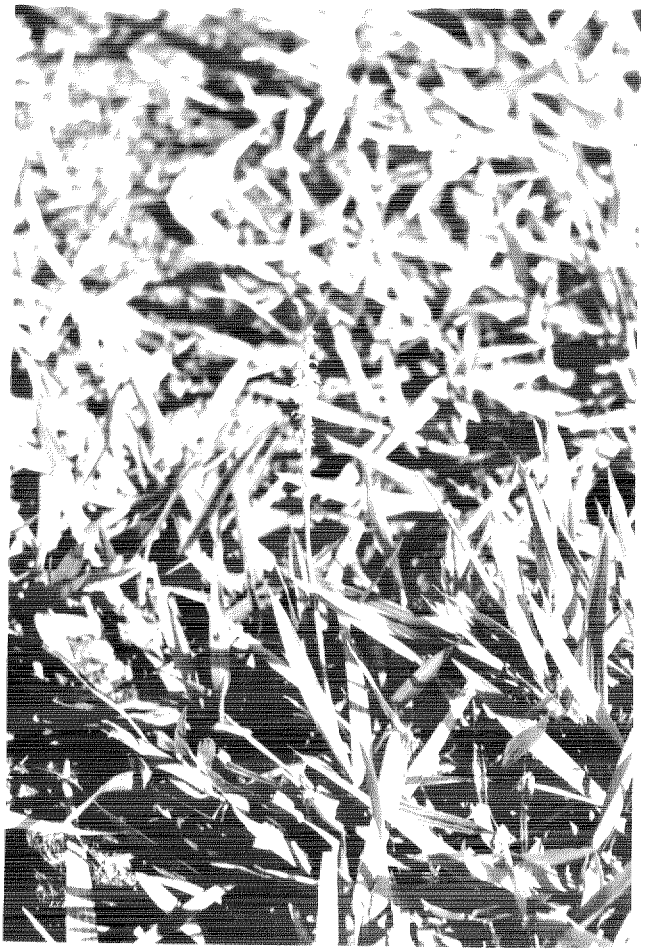
FIG. 7 shows the seedhead of 'SS-500'.
Figure 8:
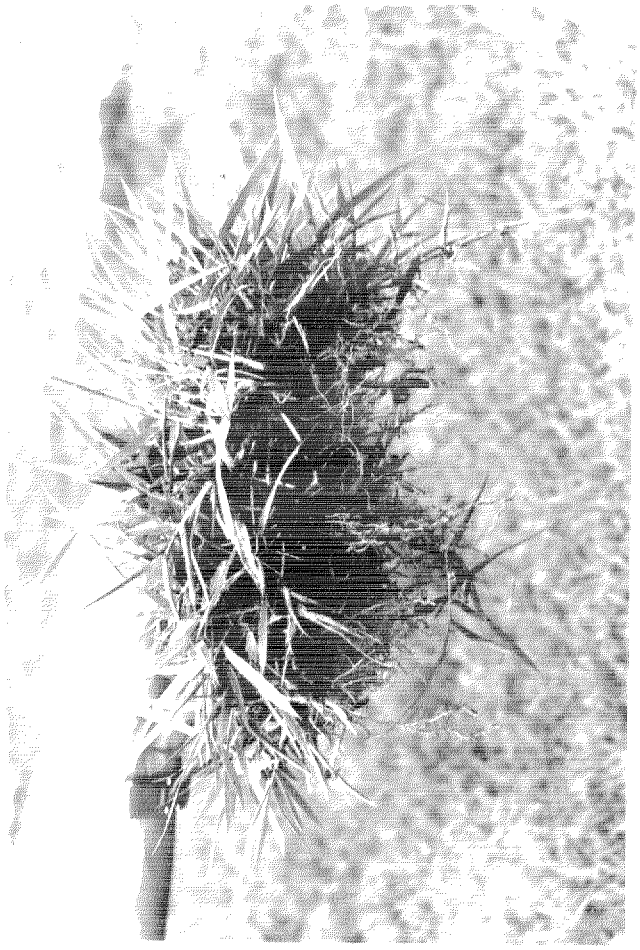
FIG. 8 shows one view of the root structure of 'SS-500'.
Figure 9:
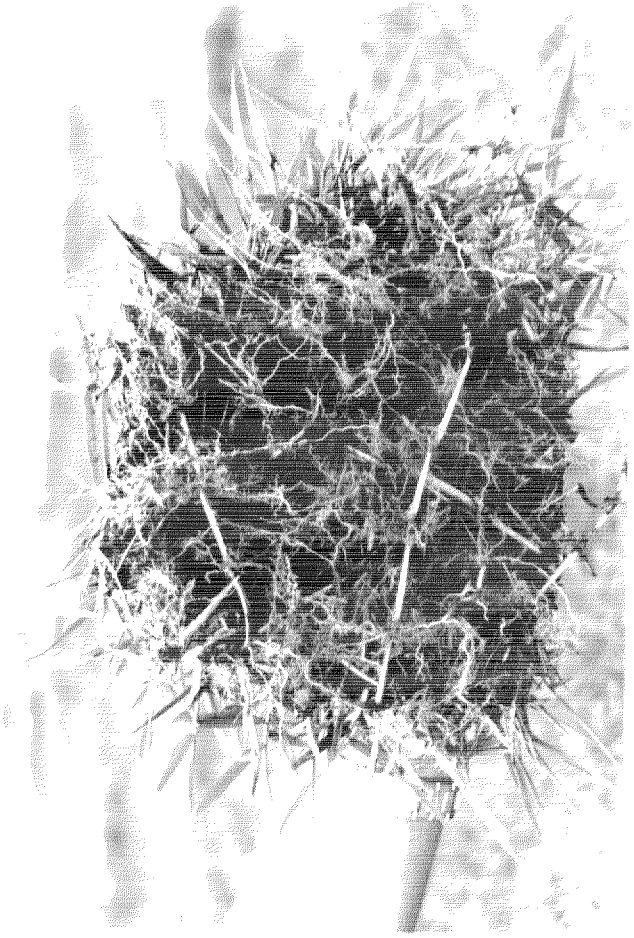
FIG. 9 shows one view of the root structure of 'SS-500'.
Figure 10:
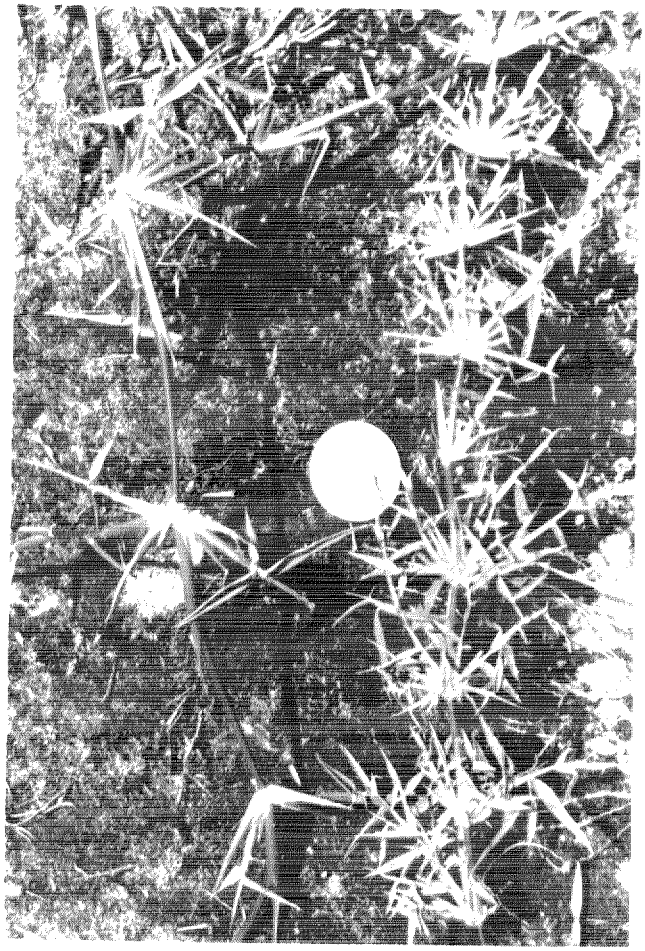
FIG. 10 provides a comparison of the 'SS-500' (top) and 'SS-300' (bottom) cultivars.
Figure 11:
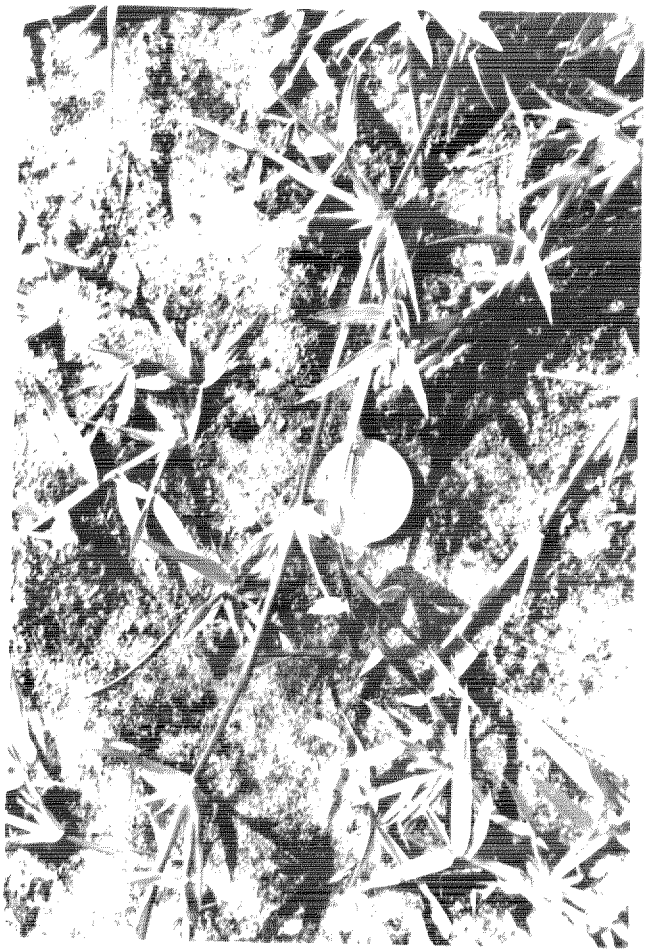
FIG. 11 shows a close-up of stem color of 'SS-500'.

The leaf blade width and length of 'SS-500' are larger than 'El Toro' or other comparable types of Zoysia. 'SS-500' has a more open growth habit, fewer seedheads, and longer as well as wider leaf blades than 'Wild Zoysia', 'El Toro' Zoysia (U.S. Plant Pat. No. 5,845), or 'Meyer' (unpatented) Zoysia. Further comparison testing to variety 'El Toro', a standard for rapid growth of Zoysia, demonstrates that 'SS-500' can exhibit 100% coverage within five to six months of planting as compared to 'El Toro', which takes nine to ten months under similar conditions. This characteristic may be beneficial to the turf industry, as providing a grass suitable for erosion control. Runners of 'SS-500' have been measured at 30 inches in length after a three-week growth period, as shown in FIG. 3. The growth and morphology of 'SS-500' is further characterized in Table I, which presents data regarding blade width, blade length, internode length, stolon width, and spike length for 'SS-500' in comparison with other varieties of Zoysia.

TABLE I

| | Length and Width Data | | | | |
|---|---|---|---|---|---|
| | Blade Width (mm) | Blade Length (mm) | Internode Length (mm) | Stolon Width (mm) | Spike Length (mm) |
| 'SS-300' | 1.9–2.3 | 30–40 | 18–25 | 1.0–1.5 | 16–18 |
| 'SS-500' | 4.7–5.5 | 120–140 | 30–35 | 2.0–2.3 | 30–40 |
| 'El Torro' | 3.0–3.2 | 42–47 | 23–27 | 1.4–1.5 | 27–30 |
| 'Meyer' | 3.1–3.6 | 39–42 | 34–38 | 1.5–1.8 | 24–28 |
| 'Emerald'* | 0.5–1.4 | 20–30 | 10–15 | 0.8–1.2 | 12–14 |

*unpatented
Reference: Test plots located at Elsberry Greenhouse in Ruskin, FL.
Reference: Test plots located at Bethel Farms in Arcadia, FL.
8' × 8' plots
Plugged by Elsberry Greenhouse in Ruskin, FL on 2/03/98.
Plugged by Bethel Farms in Arcadia, FL on 2/18/99.
Material attained by special permit USDA Quarantine Lab, Beltsville, MD.

'SS-500', unlike many Zoysia grasses, can be easily mowed with a rotary mower due to its large blade size and its open growth habitat. This trait is important as it reduces general maintenance and allows the use of less expensive mowing equipment.

'SS-500' spreads by stolons and rhizomes and forms an open uniform groundcover. The stolons are grey-purple in color (183B). Stolons are about 4 to 5 millimeters in width with nodes about 3 to 3.5 centimeters apart. The nodes of 'SS-500' root adventitiously. New leaves are rolled into bud shoots. Mature leaves are about 5 to 5.5 millimeters in width and can reach 14 centimeters in length. Mature leaves have a dark green color on both upper and lower surfaces corresponding to 137A. The leaves have hairs along the edges, which are more concentrated along the end of the leaf. The leaves taper to a point. The culm has the same dark green color (137A) as the leaf blade. The collar is large and continuous. The inflorescence is a single spike at the top of the stem. The anther is white (155D) and the stigmas are green-white (157C) in color. The seed pods are greyed purple at the top portion (i.e., tip) and fade to a green-white color at the bottom portion of the seed pod (183C and 157C, respectively). The root structure is massive and deep, with large individual roots.

'SS-500' demonstrates an extended season as compared with other Zoysia grasses. The 'SS-500' variety exhibits early greening in the Spring and late Fall color retention.

These and other features and characteristics of the 'SS-500' cultivar are apparent from the figures provided herein.

REPRODUCTION

After its initial discovery, 'SS-500' was removed from the production field and transplanted into plug trays for further trials and testing. After several series of cuttings and transplantings were made, 'SS-500' retained the color, size, and node length characteristics that were originally noted. 'SS-500' was taken transplanted to field plots for examination.

During examination of 'SS-500' transplanted to field plots, it was noted that 'SS-500' spread at a rate faster than 'Wild Zoysia' (30–40% faster). Further testing and evaluation determined that the root system of 'SS-500' is more aggressive than that of 'Wild Zoysia', and equally dense to that of 'Wild Zoysia'. Roots of 'SS-500' are generally larger in diameter than those of 'Wild Zoysia'. Further comparison testing to variety 'El Toro', a standard for rapid growth of Zoysia, demonstrates that 'SS-500' can exhibit 100% coverage within five to six months of planting, compared to 'El Toro' which takes nine to ten months under similar conditions. More extensive data regarding coverage rates of 'SS-500' in comparison with other Zoysias are presented in Table 2. Other turf characteristics are provided in Table 3 and Table 4.

TABLE 2

| | Percent Coverage Data (%) | | | | | |
|---|---|---|---|---|---|---|
| | Plant # | 30 Days | 60 Days | 90 Days | 120 Days | 150 Days |
| 'SS-300' | 20 | 30 | 40 | 55 | 80 | 95 |
| 'SS-500' | 20 | 35 | 45 | 60 | 85 | 100 |
| 'El Torro' | 20 | 25 | 35 | 50 | 65 | 80 |
| 'Meyer' | 20 | 25 | 30 | 45 | 55 | 70 |
| 'Emerald'* | 20 | 20 | 25 | 35 | 45 | 55 |

*unpatented
Reference: Test plots located at Elsberry Greenhouse in Ruskin, FL.
Reference: Test plots located at Bethel Farms in Arcadia, FL.
8' × 8' plots
Plugged by Elsberry Greenhouse in Ruskin, FL on 2/03/98.
Plugged by Bethel Farms in Arcadia, FL on 2/18/99.
Material attained by special permit USDA Quarantine Lab, Beltsville, MD.

TABLE 3

Zoysia Variety Evaluation

| | Turf Density | Seedhead Presence | Turf Color | Turf Quality | Disease Presence |
|---|---|---|---|---|---|
| 'El Toro' | 78.8 | 17.5 | 6.25 | 7.63 | 22.5 |
| 'SS-500' | 92.5 | 18.8 | 6.25 8.00 | 15.0 | |
| 'Meyer' | 36.3 | 0.0 | 8.13 | 6.25 | 58.5 |
| 'SS-300' | 93.8 | 0.0 | 6.38 | 7.38 | 53.8 |
| 'Emerald' | 17.5 | 0.0 | 7.38 | 6.63 | 58.8 |
| Rating Scale | 0–100% | 0–100% | 1–9 1 = light 9 = dark | 1–9 1 = poor 9 = good | 1–100% |
| Rating Date | 7/24/99 | 7/24/99 | 7/24/99 | 7/24/99 | 7/24/99 |

Evaluations performed at Sod Solutions Coastal Research Center, Charleston, South Carolina.

TABLE 4

Zoysia Variety Evaluation

| | Turf Quality | Stolon Regrowth | Plug Mortality | Seedhead Presence |
|---|---|---|---|---|
| 'El Toro' | 7.88 | 29.3 | 0.0 | 30.0 |
| 'SS-500' | 8.00 | 47.0 | 0.0 | 85.0 |
| 'Meyer' | 8.38 | 4.3 | 0.0 | 11.3 |
| 'SS-300' | 8.63 | 150.0 | 0.0 | 1.3 |
| 'Emerald' | 7.00 | 26.5 | 0.3 | 10.0 |
| Rating Scale | 1–9 1 = poor 9 = good | Number | Percent | 1–100% |
| Rating Date | 5/7/99 | 5/7/99 | 5/7/99 | 5/7/99 |

| | Internode Length | Blade Width | Turf Density | Plug Width |
|---|---|---|---|---|
| 'El Toro' | 26.0 | 3.20 | 7.5 | 15.47 |
| 'SS-500' | 35.0 | 5.23 | 10.0 | 15.90 |
| 'Meyer' | 34.0 | 3.10 | 0.0 | 12.60 |
| 'SS-300' | 19.0 | 2.28 | 11.3 | 15.50 |
| 'Emerald' | 12.0 | 1.20 | 1.3 | 14.22 |
| Rating Scale | mm | mm | 1–100% | cm |
| Rating Date | 5/22/99 | 5/22/99 | 5/22/99 | 5/22/99 |

Evaluations performed at Sod Solutions Coastal Research Center, Charleston, South Carolina.

Sprigs of 'SS-500' establish roots quickly, within three to six days, and the root system is massive and deep. Other advantages both physically and morphologically are apparent from the figures provided herein.

'SS-500', unlike many Zoysia grasses, can be easily mowed with a rotary mower due to its large blade size and its open growth habit. This trait reduces general maintenance and allow the use of less expensive mowing equipment.

'SS-500' can be propagated from sod, plugs, sprigs, stolons, tillers or rhizome pieces. Because 'SS-500' regrows from rhizomes, ribbons or strips of grass are not required to be left in the field for successful re-growth after sod harvesting. Seed stability is undetermined at this time, but indications suggest that there is little to no viability.

Asexual propagation of 'SS-500' was carried out in the state of São Paolo, Brazil. Asexual reproduction of 'SS-500' by rhizomes and tillers has established that the characteristics and combination of characteristics noted in 'SS-500' are transmitted during succeeding propagations.

ENVIRONMENTAL TOLERANCES

'SS-500' is similar to other *Zoysia japonica* varieties in that it requires full sun to slight shade. Its hardiness zone is unknown; cold hardiness studies are currently underway. 'SS-500' has been noted to turn brown after heavy frost, but has excellent fall color retention.

'SS-500' has good drought tolerance, most likely due to the massive root system.

DISEASE RESISTANCE AND SUSCEPTIBILITY

'SS-500' has resistance to leaf spot disease and only limited susceptibility to armyworms as compared with other grasses.

DNA FINGERPRINT ANALYSIS

DNA fingerprint analysis was carried out on 'SS-500' at the University of Tennessee using the methods described in U.S. Pat. No. 5,413,909 and by Caetano-Anolles et al., (1991) *Bio/Technology* 9:553. Cultivar 'SS-300' and standards 'Meyer', 'El Toro', and 'Emerald' (unpatented) were also analyzed. Genomic DNA was isolated from freshly grown material. No evidence of diseased tissue or weeds was detected. Several young blades of grass were ground in liquid nitrogen and DNA extracted. DNA was extracted in duplicate from the supplied samples. The DNA was quantified by fluorimetry, then was diluted and amplified using the standard high primer-low template DNA ratio using DNA amplification fingerprinting (DAF) as described in U.S. Pat. No. 5,413,909 and Caetano-Anolles et al., (1991) *Bio/Technology* 9:553. Stoffel fragment of Taq™ DNA polymerase (Perkin Elmer Corp.) was used to amplify genomic DNA. Primers 8.6i and 10.6e were used. Amplification occurred in an MJR PT200 thermocycler, using the optimized DAF amplification program DAF15. This program involves fast ramping, high annealing temperature (55° C.), and an extension step at 72° C. Resulting amplification products were resolved using SUPERGEL™ polyacrylamide gel electrophoresis (Bassam and Bentley, (1995) *Biotechniques* 19:568) and visualized by silver staining as described in U.S. Pat. No. 5,643,479 and Bassam et al., (1991) *Anal. Biochemistry* 196:80.

The DNA was extracted in duplicate from the samples. The DNA was diluted and amplified as described above. Duplicate amplification products were separated by polyacrylamide gel electrophoresis.

Figure 12:
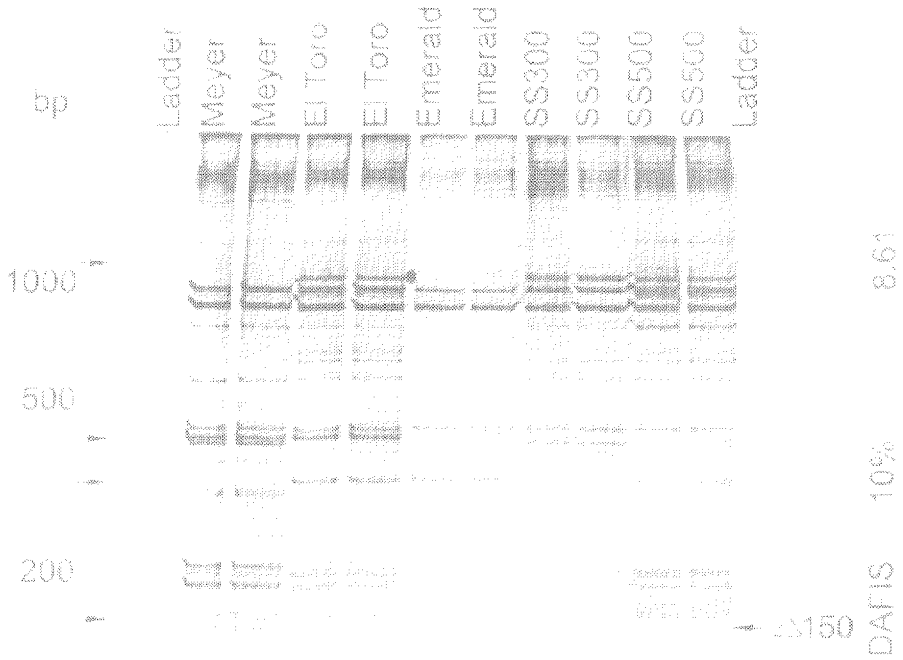
FIG. 12 is a gel showing DNA fingerprint analysis of 'SS-500' in comparison to other varieties of zoyziagrass using primer 8.6i. M=molecular size markers in base pairs. Areas of distinct DNA amplification differences are indicated by small arrows.
Figure 13:
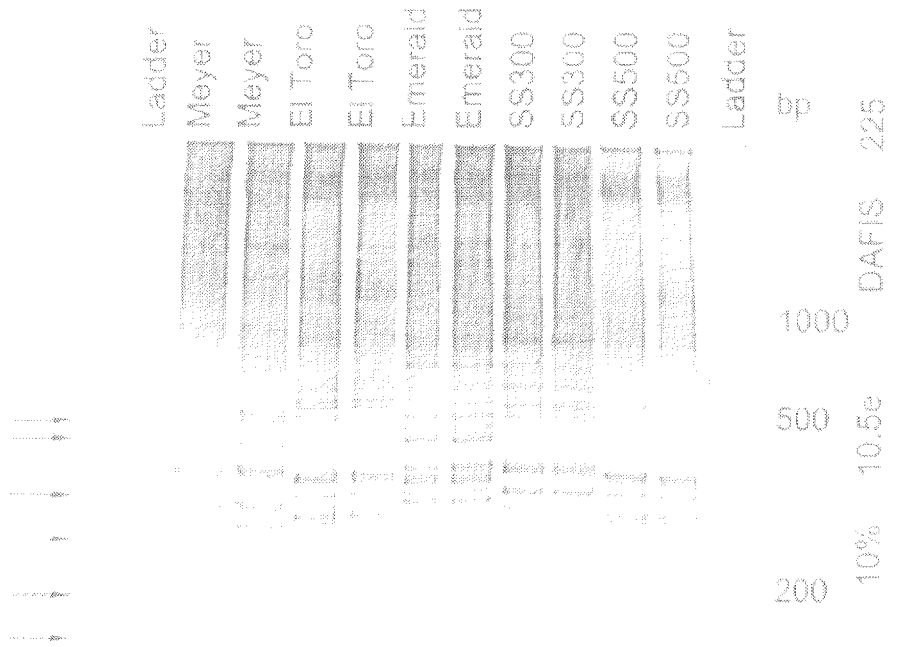
FIG. 13 is a gel showing DNA fingerprint analysis of 'SS-500' in comparison to other varieties of zoyziagrass using primer 10.6e. M=molecular size markers in base pairs. Areas of distinct DNA amplification differences are indicated by small arrows.

Two gels showing the result of DNA analysis are shown in FIG. 12 and FIG. 13, using primer 8.6i or 10.6e, respectively. About 15 major amplification products, seen as strong bands, and about 30 minor ones are commonly seen. The lanes on the sides represent molecular size markers (1000, 700, 500 (doublet), 400, 300, 200 and 100 bp) used to determine the size of the amplification products.

Using primer 8.6i (FIG. 12), several polymorphic bands were seen that distinguish 'SS-500' from the other Zoysia cultivars. The primer 8.6i clearly distinguishes the 'Meyer', 'El Toro' and 'Emerald' standards, e.g., in the 400–500 bp region.

The 'SS-300' and 'SS-500' samples are similar to each other, but clearly different. The differences between these two cultivars are even more pronounced with the 10.6e primer (FIG. 13).

The results of the fingerprinting analysis indicated that both 'SS-500' and 'SS-300' are most closely related to 'El Toro'. The 'SS-500' and 'SS-300' varieties appear to be related, but are clearly distinct from each other. Primers 8.6i and 10.6e showed clear polymorphisms for several major bands. Areas of distinct DNA amplification differences are indicated by small arrows in FIG. 12 and FIG. 13.

That which is claimed is:

1. A new and distinct variety of *Zoysia japonica* grass plant named 'SS-500', substantially as described and illustrated, which has an open growth habit, rapid coverage rate, and large leaf blades.

* * * * *